(12) United States Patent
Matsumoto et al.

(10) Patent No.: US 8,378,147 B2
(45) Date of Patent: Feb. 19, 2013

(54) PROCESS FOR PRODUCING A 2-ALKYL-2-CYCLOALKENE-1-ONE

(75) Inventors: Kunshi Matsumoto, Wakayama (JP); Atsushi Nagasawa, Wakayama (JP); Yoshiharu Ataka, Wakayama (JP)

(73) Assignee: KAO Corporation, Tokyo (JP)

(*) Notice: Subject to any disclaimer, the term of this patent is extended or adjusted under 35 U.S.C. 154(b) by 228 days.

(21) Appl. No.: 12/988,164

(22) PCT Filed: Apr. 2, 2009

(86) PCT No.: PCT/JP2009/056871
§ 371 (c)(1),
(2), (4) Date: Oct. 15, 2010

(87) PCT Pub. No.: WO2009/128347
PCT Pub. Date: Oct. 22, 2009

(65) Prior Publication Data
US 2011/0040127 A1 Feb. 17, 2011

(30) Foreign Application Priority Data

Apr. 15, 2008 (JP) ................................. 2008-105334

(51) Int. Cl.
*C07C 45/67* (2006.01)
*B01J 21/18* (2006.01)
(52) U.S. Cl. ....................... 568/341; 502/185
(58) Field of Classification Search .................. 568/341; 502/185
See application file for complete search history.

(56) References Cited

U.S. PATENT DOCUMENTS

| | | | |
|---|---|---|---|
| 4,260,830 A | | 4/1981 | Wilson et al. |
| 6,753,351 B2 * | | 6/2004 | Clark et al. ................... 518/700 |
| 7,057,077 B2 * | | 6/2006 | Nishimura et al. ........... 568/341 |
| 2003/0144130 A1 | | 7/2003 | Clark et al. |
| 2005/0014968 A1 | | 1/2005 | Mine et al. |

FOREIGN PATENT DOCUMENTS

| JP | 52-39655 | 3/1977 |
|---|---|---|
| JP | 56-147740 | 11/1981 |
| JP | 5-92934 | 4/1993 |
| JP | 2004-203844 | 7/2004 |
| JP | 2005-35939 | 2/2005 |
| JP | 2005-516769 | 6/2005 |

OTHER PUBLICATIONS

International Search Report mailed on Jul. 7, 2009 in PCT/JP2009/056871.
Kenzo Takeishi, et al., "Rhodium-Catalyzed Intramolecular Hydroacylation of 5- and 6-Alkynals: Convenient Synthesis of α-Alkylidenecycloalkanones and Cycloalkenones", Chemistry—European Journal, vol. 10, 2004, pp. 5681-5688.
Chin-Kang Sha, et al., "Synthesis of a Highly Hindered Hydrindanone via α-Carbonyl Radical Cyclization: Enantiospecific Formal Syntheses of (−)-Pinguisenol and (−)-α-Pinguisene", Journal of Organic Chemistry, vol. 68, 2003, pp. 8704-8707.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

The present invention relates to a process for producing a 2-alkyl-2-cycloalken-1-one represented by the following general formula (2), including the step of reacting a 2-alkylidene cycloalkanone in the presence of a palladium and/or platinum catalyst which is treated in the following steps (a) and (b); and a method for activating the palladium and/or platinum catalyst including the following steps (a) and (b):

Step (a): activating the palladium and/or platinum catalyst in an atmosphere containing a hydrogen gas; and Step (b): replacing the hydrogen gas being present as the atmosphere for the catalyst in the step (a), with an inert gas to remove the hydrogen gas out of the reaction system,

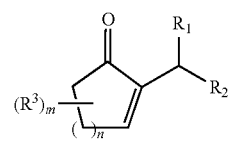

(2)

wherein m is 0 to 3; n is 1 or 2; $R^1$ and $R^2$ are each independently a hydrogen atom or an alkyl group having 1 to 8 carbon atoms; and $R^3$ is an alkyl group having 1 to 5 carbon atoms. In accordance with the present invention, the 2-alkyl-2-cycloalken-1-one can be produced with a high purity and a high productivity.

17 Claims, No Drawings

PROCESS FOR PRODUCING A 2-ALKYL-2-CYCLOALKENE-1-ONE

CROSS REFERENCES TO RELATED APPLICATIONS

This application is a 371 of International Patent Application No. PCT/JP2009/056871, filed on Apr. 2, 2009, and claims priority to Japanese Patent Application No. 2008-105334, filed on Apr. 15, 2008.

FIELD OF THE INVENTION

The present invention relates to a process for producing 2-alkyl-2-cycloalken-1-ones, and a method for activating a palladium and/or platinum catalyst.

BACKGROUND OF THE INVENTION

The 2-alkyl-2-cycloalken-1-ones are useful substances as an intermediate for synthesis of physiologically active substances or perfume materials. As the method of producing the 2-alkyl-2-cycloalken-1-ones, there are conventionally known the method in which 2-(alkylidene)cycloalkanones are subjected to isomerization reaction by contacting with a solid acid catalyst in a vapor phase under heating condition (Patent Document 1), the method in which 2-(alkylidene)cycloalkanones are subjected to isomerization reaction using a platinum group metal catalyst under heating condition (Patent Document 2), the method in which 2-(alkylidene)cycloalkanones are subjected to isomerization reaction at a temperature of from 20 to 150° C. in the presence of a hydrogen halide or sulfonic acid (Patent Document 3), and the method in which 2-(alkylidene)cycloalkanones are subjected to isomerization reaction by contacting with a hydrogen halide in an alcohol solvent at a temperature of from 150 to 190° C. (Patent Document 4).

However, the method described in Patent Document 1 has such a problem that the vapor phase reaction requires complicated procedures. In the method described in Patent Document 2, there tends to occur such a problem that a double bond is reduced by a hydrogen gas used for activation of the catalyst to produce 2-alkylcycloalkanones as by-products, which results in poor yield of the aimed 2-alkyl-2-cycloalken-1-ones and therefore fails to obtain the 2-alkyl-2-cycloalken-1-ones with a high purity. Also, the methods described in Patent Documents 3 and 4 tend to suffer from the problems such as corrosion of reaction vessels used therein and need post-treatments owing to use of a strong acid.

Patent Document 1: JP-A 55-120533
Patent Document 2: JP-B 58-42175
Patent Document 3: JP-A 51-23240
Patent Document 4: JP-A 2000-327618

SUMMARY OF THE INVENTION

The present invention relates to the following aspects [1] and [2].

[1] A process for producing a 2-alkyl-2-cycloalken-1-one represented by the following general formula (2), including the step of reacting a 2-alkylidene cycloalkanone represented by the following general formula (1) in the presence of a palladium and/or platinum catalyst which is treated in the following steps (a) and (b):

Step (a): activating the palladium and/or platinum catalyst in an atmosphere containing a hydrogen gas; and Step (b): replacing the hydrogen gas being present as the atmosphere for the catalyst in the step (a), with an inert gas to remove the hydrogen gas out of the reaction system,

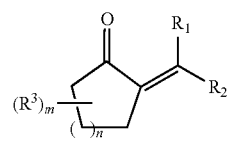

(1)

wherein m is an integer of 0 to 3; n is an integer of 1 or 2; $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto; and $R^3$ is an alkyl group having 1 to 5 carbon atoms which may be substituted for any of hydrogen atoms bonded to the alicyclic structure; and

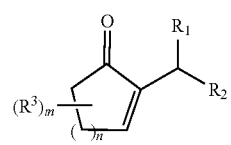

(2)

wherein m, n, $R^1$, $R^2$ and $R^3$ are the same as defined above.

[2] A method for activating a palladium and/or platinum catalyst, including the following steps (a) and (b):

Step (a): activating the palladium and/or platinum catalyst in an atmosphere containing a hydrogen gas; and Step (b): replacing the hydrogen gas being present as the atmosphere for the catalyst in the step (a), with an inert gas to remove the hydrogen gas out of the reaction system.

DETAILED DESCRIPTION OF THE INVENTION

The present invention relates to a process for producing a 2-alkyl-2-cycloalken-1-one as the aimed product with a high purity and a high productivity, and a method for activating a palladium and/or platinum catalyst.

The present inventors have found that when reacting a 2-alkylidene cycloalkanone in the presence of a palladium and/or platinum catalyst which is treated with a hydrogen gas and an inert gas, it is possible to produce a 2-alkyl-2-cycloalken-1-one with an excellent selectivity and a high yield.

The process for producing a 2-alkyl-2-cycloalken-1-one represented by the following general formula (2) (hereinafter occasionally referred to merely as a "compound (2)") according to the present invention, is characterized in that a 2-alkylidene cycloalkanone represented by the following general formula (1) (hereinafter occasionally referred to merely as a "compound (1)") is reacted in the presence of a palladium and/or platinum catalyst which is treated in the following steps (a) and (b).

In addition, the method for activating a palladium and/or platinum catalyst according to the present invention is characterized by including the following steps (a) and (b).

Step (a): activating the palladium and/or platinum catalyst in an atmosphere containing a hydrogen gas; and Step (b): replacing the hydrogen gas being present as the atmosphere for the catalyst in the step (a), with an inert gas to remove the hydrogen gas out of the reaction system.

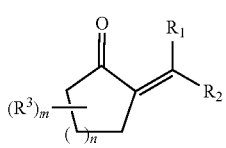

(1)

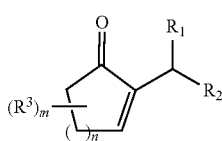

(2)

wherein m is an integer of 0 to 3; n is an integer of 1 or 2; $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto; and $R^3$ is an alkyl group having 1 to 5 carbon atoms which may be substituted for any of hydrogen atoms bonded to the alicyclic structure.

[Compounds (1) and (2)]

In the process for producing the compound (2) according to the present invention, the compound (1) is used as a raw material thereof.

In the above general formulae (1) and (2), $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto. $R^1$ and $R^2$ are each preferably a hydrogen atom or a straight-chain or branched alkyl group, and more preferably a hydrogen atom or a straight-chain alkyl group.

Examples of the alkyl group as $R^1$ and $R^2$ include a methyl group, an ethyl group, various straight-chain or branched propyl groups, various straight-chain or branched butyl groups, various straight-chain or branched pentyl groups, various straight-chain or branched hexyl groups, various straight-chain or branched heptyl groups and various straight-chain or branched octyl groups.

The clause "$R^1$ and $R^2$ may form a cyclopentane ring or a cyclohexane ring through a carbon atom adjacent thereto" as used herein means that $R^1$ may be bonded to $R^2$ through the carbon atom, or $R^2$ may be bonded to $R^1$ through the carbon atom, to form a 5-membered ring or a 6-membered ring. Meanwhile, hydrogen atoms bonded to the carbon atom may be substituted, for example, with a hydrocarbon group such as an alkyl or alkenyl group having 1 to 5 carbon atoms.

In the general formulae (1) and (2), $R^3$ is an alkyl group having 1 to 5 carbon atoms which may be substituted for any of hydrogen atoms bonded to an alicyclic structure constituting the cycloalkenone. The alkyl group having 1 to 5 carbon atoms is preferably an alkyl group having 1 to 3 carbon atoms such as a methyl group, an ethyl group and a propyl group.

The method for producing the compound (1) as the raw material is not particularly limited. For example, the compound (1) may be produced by the method described in "Chemical Abstracts", Vol. 79, 78170f, etc., in which cyclopentanone and an aldehyde are subjected to aldol condensation reaction.

Examples of the suitable compound (1) include those compounds of the general formula (1) in which m is 0; n is 1 or 2, preferably 1; and $R^1$ and $R^2$ are each independently a hydrogen atom or a straight-chain or branched alkyl group having 1 to 8 carbon atoms and preferably 3 to 6 carbon atoms.

Specific examples of the compound (1) include 2-propylidene cyclopentanone, 2-butylidene cyclopentanone, 2-(2'-methylpropylidene)cyclopentanone, 2-pentylidene cyclopentanone, 2-(2'-methylbutylidene)cyclopentanone, 2-hexylidene cyclopentanone, 2-(2'-ethylpropylidene)cyclopentanone and 2-(2'-propylpentylidene)cyclopentanone.

In the present invention, the compound (1) obtained by the above method may be used as such without subjecting it to purification. However, if the catalyst used therein are deteriorated in an activity thereof, the obtained compound (1) may also be purified before use by suitable methods such as distillation.

[Production of Compound (2)]

The compound (2) of the present invention is produced by reacting the compound (1) in the presence of a palladium and/or platinum catalyst which is treated in the following steps (a) and (b):

Step (a): activating the palladium and/or platinum catalyst in an atmosphere containing a hydrogen gas; and Step (b): replacing the hydrogen gas being present as the atmosphere for the catalyst in the step (a), with an inert gas to remove the hydrogen gas out of the reaction system.

<Catalysts>

The catalyst used in the present invention contains platinum (Pt) and/or palladium (Pd) (hereinafter occasionally totally referred to merely as "metal components") as main components. These metal components, etc., may be used alone or in combination of any two or more thereof. The term "containing the metal components as main components" as used herein means that the metal components are preferably contained in an amount of 50 mol % or more, more preferably 70 mol % or more, still more preferably 90 mol % or more, and further still more preferably 95 mol % or more on the basis of the whole metal components in the catalyst.

The catalyst may also contain other metal components or may contain a co-catalyst in an auxiliary amount. Examples of the other metal components include elements of Groups 8 and 9 in the 5th and 6th periods of the Periodic Table such as Ru, Rh, Os and Tr, and elements of Groups 4 to 11 in the 4th period of the Periodic Table such as Ti, V, Cr, Mn, Fe, Co, Ni and Cu, as well as W, Ag and Au.

The catalyst may be formed into an appropriate configuration such as a supporting type catalyst, a Raney type catalyst, a homogeneous catalyst, a powder type catalyst and a granule type catalyst, when used in the process.

The supporting type catalyst is a catalyst of such a type in which the metal components are supported on a carrier in order to improve physical properties thereof such as durability. The supporting type catalyst may be prepared by known methods such as a precipitation method, an ion exchange method, an evaporation-to-dryness method, a spray-drying method and a kneading method. Examples of the carrier include carbon (activated carbon), alumina, silica, silica-alumina, barium sulfate and calcium carbonate. Among these carriers, preferred are carbon (activated carbon), silica, alumina and silica-alumina.

Specific examples of the supporting type catalyst include palladium on carbon, platinum carbon, palladium on alumina, platinum on alumina, palladium on barium sulfate, platinum on barium sulfate, palladium on calcium carbonate and platinum on calcium carbonate. Among these catalysts, palladium on carbon, platinum on carbon, palladium on alumina and platinum on alumina are preferred because they have a high activity to the reaction, and the catalyst can be readily recovered from the reaction mixture after completion of the reaction. Among them, palladium on carbon and platinum on carbon are especially preferred from the viewpoints of a good availability, easiness of handing and a high activity to the reaction.

The amount of the metal components supported on the carrier in the supporting type catalyst is usually from about 0.1 to 70% by mass on the basis of a total amount of the carrier and the metal components supported thereon from the viewpoint of a good catalytic activity thereof.

The Raney type catalyst is a porous spongy metal catalyst, and may be prepared by the method described, for example, in Teruo KUBOMATSU and Shinichiro KOMATSU "Raney Catalysts", Kyoritsu-Shuppan (1971), etc.

When using the homogeneous catalyst, for example, a solution containing a metal salt of an inorganic acid such as nitric acid and hydrochloric acid, or a mixed solution of various metal salts, may be added dropwise to the reaction system.

Meanwhile, as the above catalysts, there may also be used commercially available products.

The amount of the catalyst used in the above process may be optimized according to the type of the reaction.

In the case of the batch type reaction, from the viewpoints of a good reactivity and economy, the catalyst is preferably used in an amount of from 0.001 to 1.5 mol %, more preferably from 0.005 to 0.5 mol % and still more preferably from 0.01 to 0.2 mol % in terms of an amount of the metal components on the basis of the compound (1) as the raw material.

The catalyst may also be used either in a suspended bed or a fixed bed.

The fixed bed reaction using a solid platinum group metal catalyst is effective for mass-production of the aimed compound because no step of separating the catalyst from the final reaction product is required.

Even in the suspended bed reaction, as far as the solid catalyst is used therein, the catalyst may be readily separated by filtration, etc., from the reaction solution, so that the thus separated catalyst can be suitably recycled. The reaction may be carried out in either a liquid phase or a vapor phase, or by either a batch method or a continuous method.

<Step (a)>

In the step (a), the palladium and/or platinum catalyst is activated in an atmosphere containing a hydrogen gas.

The concentration of the hydrogen gas in a vapor phase within an activation treatment vessel is preferably 70% by mass or more, and more preferably 90% by mass or more from the viewpoint of a good activating efficiency.

The temperature used in the activation treatment of the catalyst is preferably from 20 to 150° C., more preferably from 25 to 100° C. and still more preferably from 30 to 80° C. The reduced pressure used in the activation treatment of the catalyst is preferably from 0.5 to 100 kPa, more preferably from 5 to 70 kPa and still more preferably from 10 to 60 kPa. The time of the activation treatment is preferably from 0.5 to 2 h and more preferably from 0.75 to 1.5 h.

The activation treatment of the catalyst is preferably conducted by repeating the steps of reducing the pressure and returning to the atmospheric pressure for plural times, such as 2 to 6 times, or preferably 3 to 4 times under the hydrogen gas atmosphere.

<Step (b)>

In the step (b), the hydrogen gas being present as the atmosphere for the catalyst in the step (a) is replaced with an inert gas to remove the hydrogen gas out of the reaction system.

The step (b) may be any step in which the hydrogen gas contained in the treated palladium and/or platinum catalyst obtained in the step (a) can be rapidly discharged out of the reaction system. Therefore, the other conditions of the step (b) are not particularly limited. For example, the step (b) may be a step in which the hydrogen gas is replaced with the inert gas under a slightly reduced pressure, etc.

Examples of the preferred inert gas include a nitrogen gas, an argon gas and a helium gas. Among these inert gases, more preferred is a nitrogen gas. The reduced pressure is preferably from 0.5 to 100 kPa, more preferably from 10 to 90 kPa and still more preferably from 20 to 80 kPa.

The hydrogen concentration in the vapor phase within the treatment vessel after being replaced with the inert gas is preferably from 0 to 30% by mass and more preferably from 0.1 to 10% by mass from the viewpoint of a good yield of the aimed compound.

The removal of the hydrogen gas contained in the catalyst is preferably conducted by repeating the steps of reducing the pressure and returning to the atmospheric pressure for plural times, such as 2 to 10 times, or preferably 3 to 9 times under the inert gas atmosphere.

(Reaction Conditions)

The temperature used in the reaction of the present invention is preferably from 100 to 300° C. The reaction temperature is more preferably from 150 to 250° C., still more preferably from 160 to 230° C., and especially preferably from 170 to 210° C., from the viewpoints of completing the reaction for a short period of time and preventing polymerization of the compound (1) and lowering in yield of the aimed compound.

The reaction pressure may be appropriately controlled depending upon the reaction temperature used, and is preferably in the range of from 50 to 200 kPa and more preferably from 100 to 150 kPa.

<Solvent>

The process of the present invention may be carried out either in the presence of a solvent or under a solvent-free condition. The process of the present invention is advantageously carried out under a solvent-free condition from the viewpoints of a good productivity and economy. The solvent used in the process of the present invention is not particularly limited. Examples of the solvent include alcohols such as methanol, ethanol, isopropanol, tert-butanol, n-butanol, hexanol, octanol, ethylene glycol, propylene glycol, ethylene glycol monoethyl ether, diethylene glycol and benzyl alcohol; ketones such as methyl ethyl ketone, methyl butyl ketone, cyclopentanone and cyclohexanone; ethers such as isopropyl ether, n-butyl ether, 1,4-dioxane and tetrahydropyran; esters such as n-methyl formate, methyl acetate and ethyl acetate; and hydrocarbons such as n-hexane, n-octane, n-decane, cyclohexane, benzene, toluene and xylene. These solvents may be used alone or in combination of any two or more thereof.

In the process for producing the compound (2) according to the present invention, it is possible to prevent polymerization of the 2-alkylidene cycloalkanone as the raw material and the 2-alkyl-2-cyclopentenone as the reaction product, so that the compound (2) can be produced with a high yield and a high purity. In addition, it is possible to produce the aimed compound by using the catalyst having a low corrosiveness and a low toxicity.

Examples of the suitable compound (2) in which m is 0; n is 1 or 2, preferably 1; and $R^1$ and $R^2$ are each independently a hydrogen atom or a straight-chain or branched alkyl group having 1 to 8 carbon atoms and preferably 3 to 6 carbon atoms.

Specific examples of the compound (2) include 2-propyl-2-cyclopenten-1-one, 2-isopropyl-2-cyclopenten-1-one, 2-n-butyl-2-cyclopenten-1-one, 2-n-pentyl-2-cyclopenten-1- one, 2-isopentyl-2-cyclopenten-1-one, 2-(2'-methylbutyl)-2-cyclopenten-1-one and 2-hexyl-2-cyclopenten-1-one.

Process for Producing
Alkyl(3-oxo-2-alkylcycloalkyl)acetate

The alkyl(3-oxo-2-alkylcycloalkyl)acetate represented by the following general formula (3) (hereinafter referred to merely as a "compound (3)") is a useful compound as a perfume material or a physiologically active substance, and is produced by reacting the compound (2) obtained by the above production process as the raw material in the presence of a basic catalyst.

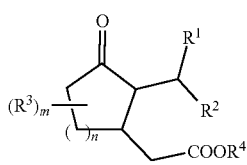
(3)

wherein m, n, $R^1$, $R^2$ and $R^3$ are the same as defined above; and $R^4$ is an alkyl group having 1 to 3 carbon atoms, preferably a straight-chain or branched alkyl group having 1 to 3 carbon atoms.

Upon production of the compound (3), the compound (2) as the raw material is first reacted with a malonic acid diester represented by the following general formula (4) in the presence of a basic catalyst under such a condition that the malonic acid diester is preferably present in an amount of from 1 to 5 mol and more preferably from 1.2 to 2 mol per 1 mol of the compound (2) to obtain a compound represented by the following general formula (5) (hereinafter referred to merely as a "compound (5)").

$$\begin{array}{c} COOR^4 \\ | \\ CH_2 \\ | \\ COOR^4 \end{array}$$
(4)

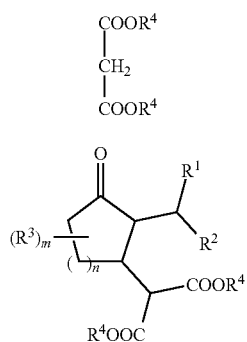
(5)

wherein m, n, $R^1$, $R^2$, $R^3$ and $R^4$ are the same as defined above, and the two $R^4$ groups may be the same or different from each other.

Examples of the basic catalyst used in the above reaction include alkali metals such as sodium and potassium; and alkali metal alkoxides such as sodium alkoxides and potassium alkoxides.

The amount of the basic catalyst used is preferably from 0.005 to 0.2 time moles and more preferably from 0.01 to 0.1 time moles per 1 mol of the compound (2) used. Examples of the preferred solvent if used include polar solvents such as alcohols.

The reaction temperature used in the above reaction is preferably from −10 to 30° C. and more preferably from −2 to 20° C.

Next, the compound (5) thus obtained by the above method is reacted with water to produce the compound (3). The amount of water to be reacted is preferably from 1 to 3 times moles per 1 mol of the compound (5) used. The reaction is preferably carried out while adding water dropwise into the reaction system. In this case, the reaction temperature is preferably from 150 to 230° C. and more preferably from 180 to 220° C.

In accordance with the present invention, the aimed compound can be produced with a high purity, and there are provided the process for producing the 2-alkyl-2-cycloalken-1-one with a high productivity, and a method for activating a palladium and/or platinum catalyst.

Further, in accordance with the present invention, since polymerization of the raw material and production of 2-alkyl cycloalkanone as a by-product are effectively prevented as compared to the conventional methods, it is possible to produced the aimed compound with a high yield and a high purity using the catalyst having a less corrosiveness and a low toxicity.

EXAMPLES

In the following Examples and Comparative Examples, the quantitative determination of respective reaction products was carried out by gas chromatography (GC) ("6890N" with a column "DB-1" (30 m×0.25 mm×0.25 μm) available from Agilent Technology Corp.; oven: 100° C.→5° C./min→210° C.→20° C./min→280° C. (held for 4.5 min) (total 30 min); carrier: He; flow rate: 1.6 mL/min; inlet temperature: 280° C.; detector (FID) temperature: 280° C.; amount charged: 1 μL; split: 100:1) according to an internal standard method (internal standard: undecane (purity: 99%; available from Nacalai Tesque, Inc.)).

Meanwhile, in the following Examples and Comparative Examples, the term "%" represents "% by mass" unless otherwise specified. In addition, all of the reaction pressures used hereinafter represent 101 kPa (atmospheric pressure).

Synthesis Examples 1

Synthesis of 2-pentylidene cyclopentanone

A 6 m³ reaction vessel equipped with a dropping vessel was charged with 2241 kg (26.6 kmol) of cyclopentanone, 1007 kg of water and 11 kg of 48% NaOH. The contents of the reaction vessel were cooled to 15° C. while stirring, and then 985 kg (11.4 kmol) of valeraldehyde were added dropwise thereto at the same temperature over 5 h, followed by stirring the resulting mixture for 1 h. After completion of the reaction, the obtained reaction mixture was neutralized, and an excess amount of cyclopentanone was recovered therefrom by distillation. As a result, it was confirmed that 1868 kg of the final reaction product obtained from an organic layer of the reaction mixture contained 1706 kg of 2-(1-hydroxypentyl)-cyclopentanone.

A 300 mL four-necked flask equipped with a dehydration apparatus was charged with 170 g (0.99 mol) of 2-(1-hydroxypentyl)-cyclopentanone obtained by purifying the above obtained final reaction product, and 8.5 g of $TiO_2$ (spherical molded product; diameter: 1.5 mm), and the contents of the flask were heated and mixed with each other at 100° C. and 53 kPa, thereby obtaining 141 g of 2-pentylidene cyclopentanone (yield: 93%).

Example 1

An organic synthesizer ("Chemi-200" available from Shibata Scientific Technology Ltd.; 100 mL glass reaction vessel) was charged with 5.0 g (0.035 mol) of decane (guaranteed reagent available from Wako Pure Chemical Industries, Ltd.; purity: 99%) and 0.43 g of 5% Pd/C (available from N.E. ChemCat Corp.; Pd carbon powder, 49% hydrous product), and an inside atmosphere of the reaction vessel was replaced with nitrogen under slightly reduced pressure (27 kPa) while stirring the contents thereof at a rate of 400 r/min. Thereafter, a pressure balloon filled with hydrogen was attached to the reaction vessel, and a procedure of controlling an inside pressure of the reaction vessel to a reduced pressure of 27 kPa and then returning the inside pressure to atmospheric pressure with the hydrogen was repeated four times. The inside temperature of the reaction vessel was raised to 50° C. at which the catalyst was activated for 1 h. Then, after a procedure of controlling an inside pressure of the reaction vessel to a reduced pressure of 54 kPa and then returning the inside pressure to atmospheric pressure with nitrogen was repeated 8 times, the inside temperature of the reaction vessel was raised to 190° C. at which 10 g of 2-pentylidene cyclopentanone (purity: 96%) obtained in Synthesis Example 1 were added to the reaction vessel using a syringe. The reaction was carried out for 6 h. As a result of analyzing the obtained reaction product by GC, it was confirmed that the internal standard-based yield of 2-pentyl-2-cyclopenten-1-one was 96%, and 2-pentyl cyclopentanone and high-boiling by-products were produced in amounts of 3% and 1%, respectively.

Example 2

The same organic synthesizer as used in Example 1 was charged with 5.0 g (0.035 mol) of decane and 1.11 g of 2% Pt/C (available from N.E. ChemCat Corp.; Pt carbon powder, 54% hydrous product). While stirring the contents of the reaction vessel at a rate of 400 r/min, a procedure of controlling an inside pressure of the reaction vessel to a reduced pressure of 27 kPa and then returning the inside pressure to atmospheric pressure with hydrogen was repeated four times. The inside temperature of the reaction vessel was raised to 50° C. at which the catalyst was activated for 1 h. Then, after a procedure of controlling an inside pressure of the reaction vessel to a reduced pressure of 54 kPa and then returning the inside pressure to atmospheric pressure with nitrogen was repeated 8 times, the inside temperature of the reaction vessel was raised to 200° C. at which 10 g of 2-pentylidene cyclopentanone (purity: 96%) obtained in Synthesis Example 1 were added to the reaction vessel using a syringe. The reaction was carried out for 6 h. As a result of analyzing the obtained reaction product by GC, it was confirmed that the internal standard-based yield of 2-pentyl-2-cyclopenten-1-one was 95%, and 2-pentyl cyclopentanone and high-boiling by-products were produced in amounts of 2% and 1%, respectively.

Comparative Example 1

The same organic synthesizer as used in Example 1 was charged with 10 g of 2-pentylidene cyclopentanone and 0.23 g of the same 5% Pd/C as used in Example 1, and an inside atmosphere of the reaction vessel was replaced with nitrogen under slightly reduced pressure (27 kPa) while stirring the contents thereof. Thereafter, a pressure balloon filled with hydrogen was attached to the reaction vessel, and after a procedure of controlling an inside pressure of the reaction vessel to a reduced pressure of 27 kPa and then returning the inside pressure to atmospheric pressure with the hydrogen was repeated four times, the inside temperature of the reaction vessel was raised to 130° C. at which the reaction was conducted for 2 h. As a result of analyzing the obtained reaction product by GC, it was confirmed that the internal standard-based yield of 2-pentyl-2-cyclopenten-1-one was 77%, and 2-pentyl cyclopentanone and high-boiling by-products were produced in amounts of 20% and 1%, respectively.

Comparative Example 2

The same organic synthesizer as used in Example 1 was charged with 10 g of 2-pentylidene cyclopentanone and 0.43 g of the same 5% Pd/C as used in Example 1, and an inside atmosphere of the reaction vessel was replaced with nitrogen under slightly reduced pressure (27 kPa) while stirring the contents thereof, and then the inside temperature of the reaction vessel was raised to 195° C. at which the reaction was conducted for 6 h. As a result of analyzing the obtained reaction product by GC, it was confirmed that the internal standard-based yield of 2-pentyl-2-cyclopenten-1-one was 85%, and 2-pentyl cyclopentanone and high-boiling by-products were produced in amounts of 4% and 11%, respectively.

Comparative Example 3

The same organic synthesizer as used in Example 1 was charged with 5.0 g (0.035 mol) of decane and 0.56 g of 5% Ir/C (available from N.E. ChemCat Corp.; Ir carbon powder, 61% hydrous product). While stirring the contents of the reaction vessel at a rate of 400 r/min, a procedure of controlling an inside pressure of the reaction vessel to a reduced pressure of 27 kPa and then returning the inside pressure to atmospheric pressure with hydrogen was repeated four times. The inside temperature of the reaction vessel was raised to 50° C. at which the catalyst was activated for 1 h. Then, after a procedure of controlling an inside pressure of the reaction vessel to a reduced pressure of 54 kPa and then returning the inside pressure to atmospheric pressure with nitrogen was repeated 8 times, the inside temperature of the reaction vessel was raised to 200° C. at which 10 g of 2-pentylidene cyclopentanone (purity: 96%) obtained in Synthesis Example 1 were added to the reaction vessel using a syringe. The reaction was carried out for 5.5 h. As a result of analyzing the obtained reaction product by GC, it was confirmed that the internal standard-based yield of 2-pentyl-2-cyclopenten-1-one was 19%, no 2-pentyl cyclopentanone was detected, and high-boiling by-products were produced in an amount of 19%.

Comparative Example 4

The same organic synthesizer as used in Example 1 was charged with 5.0 g (0.035 mol) of decane and 0.47 g of 5% Rh/C (available from N.E. ChemCat Corp.; Rh carbon powder, 54% hydrous product). While stirring the contents of the reaction vessel at a rate of 400 r/min, a procedure of controlling an inside pressure of the reaction vessel to a reduced pressure of 27 kPa and then returning the inside pressure to atmospheric pressure with hydrogen was repeated four times. The inside temperature of the reaction vessel was raised to 50° C. at which the catalyst was activated for 1 h. Then, after a procedure of controlling an inside pressure of the reaction vessel to a reduced pressure of 54 kPa and then returning the inside pressure to atmospheric pressure with nitrogen was repeated 8 times, the inside temperature of the reaction vessel was raised to 200° C. at which 10 g of 2-pentylidene cyclopentanone (purity: 96%) obtained in Synthesis Example 1 were added to the reaction vessel using a syringe. The reaction was carried out for 4 h. As a result of analyzing the obtained reaction product by GC, it was confirmed that the internal standard-based yield of 2-pentyl-2-cyclopenten-1-one was 10%, no 2-pentyl cyclopentanone was detected, and high-boiling by-products were produced in an amount of 19%.

Comparative Example 5

The same organic synthesizer as used in Example 1 was charged with 5.0 g (0.035 mol) of decane and 0.44 g of 5% Ru/C (available from N.E. ChemCat Corp.; Ru carbon powder, 50% hydrous product). While stirring the contents of the reaction vessel at a rate of 400 r/min, a procedure of controlling an inside pressure of the reaction vessel to a reduced pressure of 27 kPa and then returning the inside pressure to atmospheric pressure with hydrogen was repeated four times. The inside temperature of the reaction vessel was raised to 50° C. at which the catalyst was activated for 1 h. Then, after a procedure of controlling an inside pressure of the reaction vessel to a reduced pressure of 54 kPa and then returning the inside pressure to atmospheric pressure with nitrogen was repeated 8 times, the inside temperature of the reaction vessel was raised to 200° C. at which 10 g of 2-pentylidene cyclopentanone (purity: 96%) obtained in Synthesis Example 1 were added to the reaction vessel using a syringe. The reaction was carried out for 4 h. As a result of analyzing the obtained reaction product by GC, it was confirmed that the internal standard-based yield of 2-pentyl-2-cyclopenten-1-one was 1%, no 2-pentyl cyclopentanone was detected, and high-boiling by-products were produced in an amount of 22%.

INDUSTRIAL APPLICABILITY

In accordance with the production process of the present invention, it is possible to produce a 2-alkyl-2-cycloalken-1-one with a high yield in an industrially advantageous manner.

The invention claimed is:

1. A process for producing a 2-alkyl-2-cycloalken-1-one represented by formula (2), comprising:
   (a): activating a palladium and/or platinum catalyst in an atmosphere comprising a hydrogen gas, in a reaction system, to obtain an activated palladium and/or platinum catalyst;
   (b): replacing said hydrogen gas in said atmosphere for said activating of said palladium and/or platinum catalyst in step (a), with an inert gas to remove hydrogen gas from said reaction system; and
   (c): contacting a 2-alkylidene cycloalkanone represented by formula (1) with said activated palladium and/or platinum catalyst in said reaction system from which hydrogen has been removed,

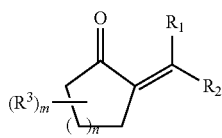
(1)

wherein m is an integer of 0 to 3; n is an integer of 1 or 2; $R^1$ and $R^2$ are each independently a hydrogen atom or an alkyl group having 1 to 8 carbon atoms, with the proviso that $R^1$ and $R^2$ together with the carbon atom to which they are bonded may form a cyclopentane ring or a cyclohexane ring; and each $R^3$ is independently an alkyl group having 1 to 5 carbon atoms which may be substituted for any of hydrogen atoms bonded to the alicyclic structure; and

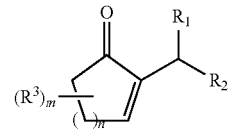
(2)

wherein m, n, $R^1$, $R^2$ and $R^3$ are the same as defined above.

2. The process according to claim 1, wherein in formulae (1) and (2), m is 0; n is 1 or 2; and $R^1$ and $R^2$ are each independently a hydrogen atom or a straight-chain or branched alkyl group having 1 to 8 carbon atoms.

3. The process according to claim 1, wherein in formulae (1) and (2), m is 0; n is 1; and $R^1$ and $R^2$ are each independently a hydrogen atom or a straight-chain or branched alkyl group having 1 to 8 carbon atoms.

4. The process according to claim 1, wherein said inert gas comprises nitrogen, argon, or helium.

5. The process according to claim 2, wherein said inert gas comprises nitrogen, argon, or helium.

6. The process according to claim 3, wherein said inert gas comprises nitrogen, argon, or helium.

7. The process according to claim 1, wherein said palladium and/or platinum catalyst is selected from the group consisting of palladium on carbon, platinum carbon, palladium on alumina, platinum on alumina, palladium on barium sulfate, platinum on barium sulfate, palladium on calcium carbonate, and platinum on calcium carbonate.

8. The process according to claim 1, wherein said activated palladium and/or platinum catalyst is contacted with said 2-alkylidene cycloalkanone represented by formula (1) in an amount of from 0.001 to 1.5 mol %, in terms of an amount of metal components of said activated palladium and/or platinum catalyst, based on the moles of said 2-alkylidene cycloalkanone represented by formula (1).

9. The process according to claim 1, wherein said activated palladium and/or platinum catalyst is contacted with said 2-alkylidene cycloalkanone represented by formula (1) in an amount of from 0.005 to 0.5 mol %, in terms of an amount of metal components of said activated palladium and/or platinum catalyst, based on the moles of said 2-alkylidene cycloalkanone represented by formula (1).

10. The process according to claim 1, wherein said activated palladium and/or platinum catalyst is contacted with said 2-alkylidene cycloalkanone represented by formula (1) in an amount of from 0.01 to 0.2 mol %, in terms of an amount of metal components of said activated palladium and/or platinum catalyst, based on the moles of said 2-alkylidene cycloalkanone represented by formula (1).

11. The process according to claim 1, wherein said activating is conducted at a temperature of from 20 to 150° C., at a pressure of from 0.5 to 100 kPa, and for a time of from 0.5 to 2 hours.

12. The process according to claim 1, wherein said activating is conducted at a temperature of from 25 to 100° C., at a pressure of from 5 to 70 kPa, and for a time of from 0.75 to 1.5 hours.

13. The process according to claim 1, wherein said activating is conducted at a temperature of from 30 to 80° C., at a pressure of from 10 to 60 kPa, for a time of from 0.75 to 1.5 hours.

14. The process according to claim 1, wherein said contacting is conducted at a temperature of from 100 to 300° C.

15. The process according to claim 1, wherein said contacting is conducted at a temperature of from 150 to 250° C.

16. The process according to claim 1, wherein said contacting is conducted at a temperature of from 160 to 230° C.

17. The process according to claim 1, wherein said contacting is conducted at a temperature of from 170 to 210° C.

* * * * *